(12) United States Patent
Zhong et al.

(10) Patent No.: US 7,119,100 B2
(45) Date of Patent: Oct. 10, 2006

(54) ORIPAVINE DERIVATIVES AND THEIR USES AS PHARMACEUTICALS

(75) Inventors: Bohua Zhong, Beijing (CN); Zehui Gong, Beijing (CN); Yaping Wang, Beijing (CN); Yongshao Liu, Beijing (CN)

(73) Assignees: Institute of Pharmacology and Toxicology Academy of Military Medical Sciences, P.L.A. China, Beijing (CN); Zhejiang Xianju Pharmaceuticals Co. Ltd., Zhejiang (CN)

( * ) Notice: Subject to any disclaimer, the term of this patent is extended or adjusted under 35 U.S.C. 154(b) by 0 days.

(21) Appl. No.: 10/489,656

(22) PCT Filed: Sep. 13, 2002

(86) PCT No.: PCT/CN02/00642

§ 371 (c)(1),
(2), (4) Date: Nov. 23, 2004

(87) PCT Pub. No.: WO03/024972

PCT Pub. Date: Mar. 27, 2003

(65) Prior Publication Data

US 2005/0070564 A1   Mar. 31, 2005

(30) Foreign Application Priority Data

Sep. 14, 2001 (CN) .................. 01 1 42149

(51) Int. Cl.
  *A61K 31/44*  (2006.01)
(52) U.S. Cl. .................. 514/279; 546/39
(58) Field of Classification Search .......... 546/39; 514/279
See application file for complete search history.

(56) References Cited

U.S. PATENT DOCUMENTS

| 3,433,791 A |   | 3/1969 | Bentley | 260/285 |
| 3,442,900 A | * | 5/1969 | Bentley | 546/39 |
| 3,474,101 A | * | 10/1969 | Bentley | 546/39 |
| 5,849,915 A | * | 12/1998 | Kim et al. | 546/39 |

OTHER PUBLICATIONS

Huang, Comparison of pharmacological Activities of Buprenorphine and Norbuprenorphine: Norbuprenorphine is a Potent Opiod Agonist, J. Pharmacology and Experimental Therapeutics, 297(2), (2001), 688-695.*

* cited by examiner

*Primary Examiner*—Amelia A. Owens
(74) *Attorney, Agent, or Firm*—Seed IP Law Group PLLC

(57) ABSTRACT

The present invention relates to oripavine derivatives of formula (I),

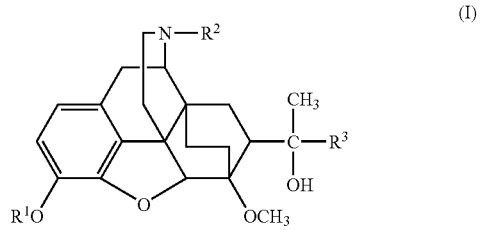

wherein $R^1$ is hydrogen or methyl, $R^2$ is methyl, cyclopropyl methyl, cyclobutyl methyl or allyl, $R^3$ is thiophenyl ethyl or cycloalkyl methyl where the cycloalkyl has 3 to 6 carbon atoms, or non-toxic pharmaceutically acceptable salts thereof. These compounds can be used for the preparation of analgesics or abstinence agents of opium habit-forming drugs.

8 Claims, 1 Drawing Sheet

ORIPAVINE DERIVATIVES AND THEIR USES AS PHARMACEUTICALS

FIELD OF THE INVENTION

The present invention relates to novel oripavine derivatives, their non-toxic pharmaceutically acceptable salts, and their uses in the preparation of analgesics or abstinence agents of opium habit-forming drugs.

BACKGROUND ART

The Great Britain patent 1136214 disclosed compounds represented by the following formula:

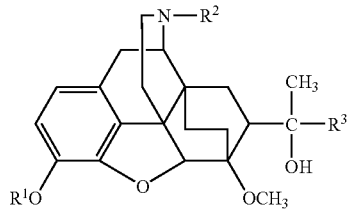

wherein $R^1$ is hydrogen or methyl, $R^2$ is cyclopropyl methyl or allyl, $R^3$ is alkyl, phenyl or phenyl alkyl. These compounds have potent central analgesic activity and opiate antagonist activity.

Among them, buprenorphine (where $R^1$ is hydrogen, $R^2$ is cyclopropyl methyl, $R^3$ is tert-butyl) has good analgesic activity and little dependence with potency 25–30 times as that of morphine and less dependence. It has now been widely used as analgesics and anti-addiction. But buprenorphine only have moderate efficacy (40% that of morphine) and low bioavailability. So it could not be administered orally.

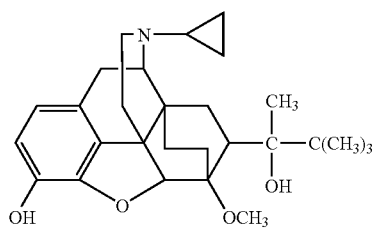

Buprenorphine

U.S. Pat. No. 3,931,189 disclosed buprenorphine analogues wherein $R^2$ is aromatic heterocyclic alkyl; Chinese patent CN1168377A disclosed buprenorphine analogues wherein $R^3$ is cyclobutyl or cyclopropyl.

Although the prior arts have given these teachings, it is still of great need for new drugs for the treatment of pain and addiction.

DETAILED DESCRIPTION OF THE INVENTION

The inventor of the present invention has discovered that the oripavine derivatives represented by the formula (I) or their pharmaceutically acceptable salts not only have strong analgesic potency and analgesic efficacy, but also exhibit good oral bioavailability, long acting time, low small animal body dependency. As a result, the invention has been completed.

Therefore, the present invention at one aspect aims to provide novel oripavine derivatives represented by the formula (I) and their non-toxic pharmaceutically acceptable salts.

The present invention at another aspect relates to a pharmaceutical composition comprising as active ingredient oripavine derivatives represented by the formula (I) and their non-toxic pharmaceutically acceptable salts and pharmaceutically acceptable carriers.

The present invention relates to oripavine derivatives represented by the formula (I):

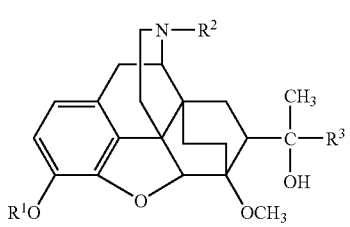

wherein $R^1$ is hydrogen or methyl, $R^2$ is methyl, cyclopropyl methyl, cyclobutyl methyl or allyl, $R^3$ is thiophenylethyl or cycloalkyl methyl where the cycloalkyl has 3 to 6 carbon atoms, and their non-toxic pharmaceutically acceptable salts.

The compounds of the formula I are preferably selected from the compounds represented by the following formulae:

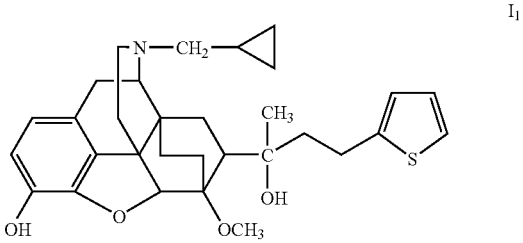

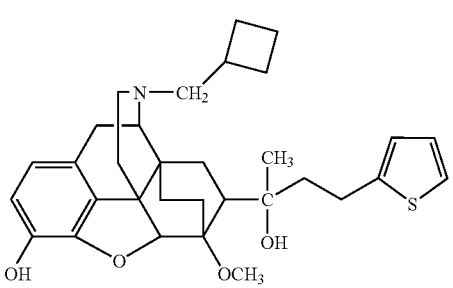

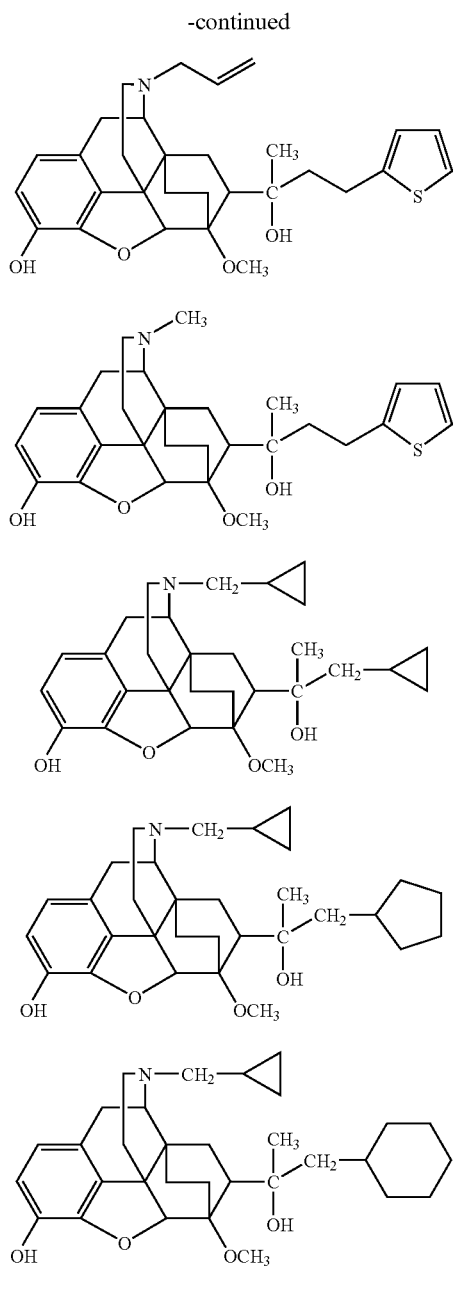
or their non-toxic pharmaceutically acceptable salts.
The oripavine derivatives according to the present invention can be prepared by the following reaction schemes:
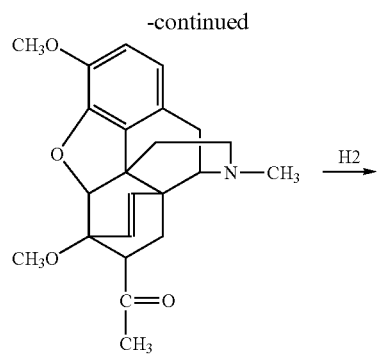
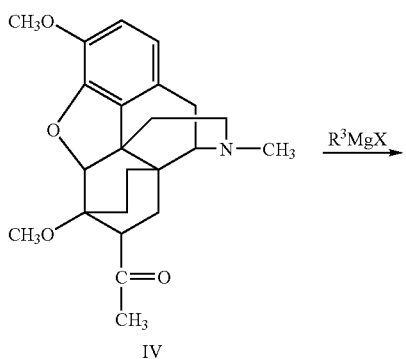
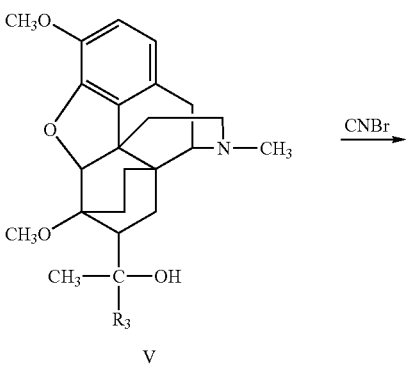
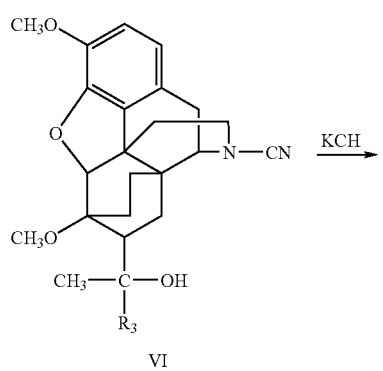

-continued

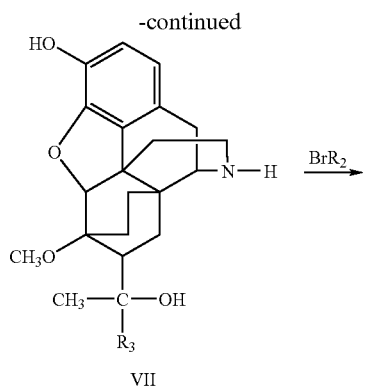

VII

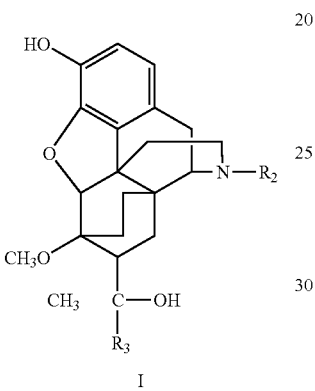

I

Starting material thebaine (II) is reacted with methyl vinyl ketone by Diels-Alder reaction to obtain a compound of formula III with a yield of 80–90%; the resulting compound of formula III is hydrogenated in the presence of palladium catalyst to obtain a compound of formula IV, the resulting compound of formula IV is reacted thiophenylethyl bromide by Grignard addition reaction to obtain a compound of formula V; the compound of formula V is reacted with cyanobromide to give the compound of formula VI substituted by N-cyano group, the compound of formula VI is hydrolyzed with potassium hydroxide to obtain a compound of formula VII, which is a key intermediate. Finally the compound of formula VII is subjected alkylation reaction on nitrogen atom to yield the target compound.

The compounds of the invention wherein $R^3$ is cycloalkyl methyl where the cycloalkyl has 3 to 6 carbon atoms can be prepared by the following schemes:

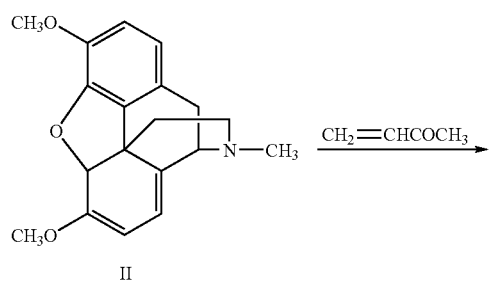

II

-continued

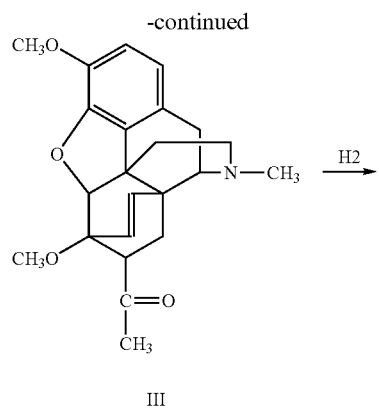

III

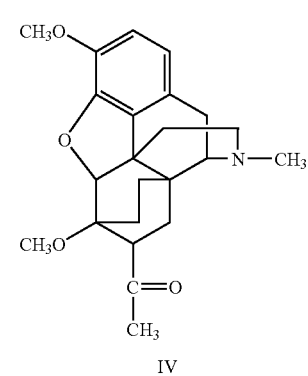

IV

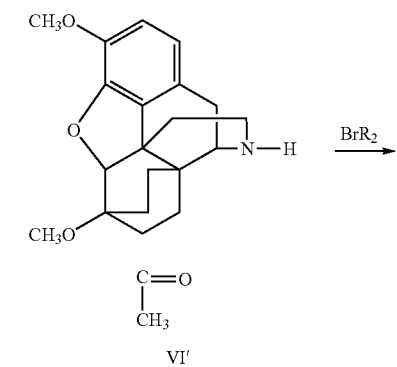

V'

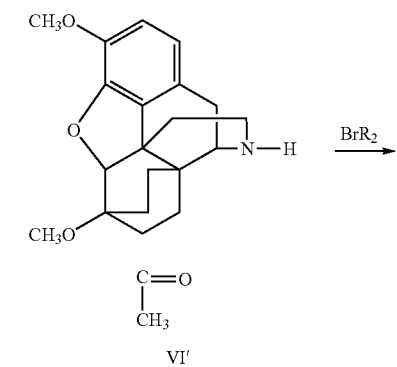

VI'

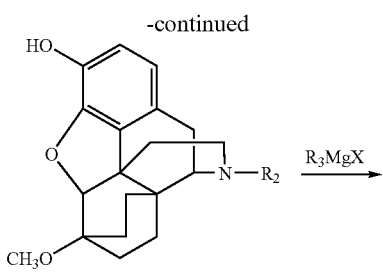

VII'

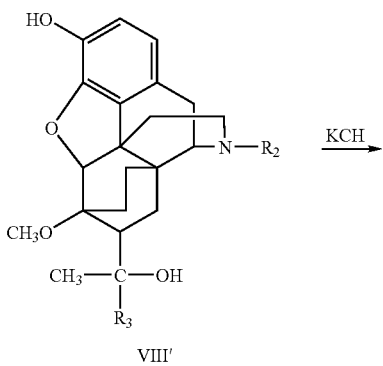

VIII'

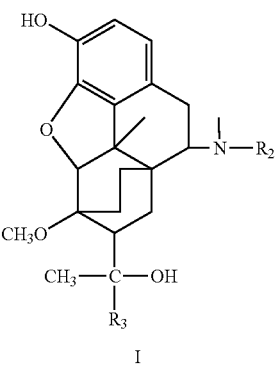

I the intermediate of formula VI obtained according to the first scheme is reacted with cyanobromide to obtain a compound of formula V' substituted by N-cyano group, the resulting compound of formula V' is hydrolyzed with potassium hydroxide to obtain a compound of VI'; the resulting compound of formula VI' is reacted with cyclopropyl methyl bromide to obtain an intermediate of formula VII'; the intermediate of formula VII' is subjected to Grignard addition reaction and then demethoxylated to yield target compound of formula I.

When a compound has sufficient acidic strength or basic capability to form a stable a nontoxic acidic or basic salt, it is appropriate that the compound is administered in the form of a salt. Examples of pharmaceutically acceptable salts are organic addition salts formed with acids, these acids form physiologically acceptable anions, such as tosylates, methyl sulfonates, acetates, citrates, malonates, tartrates, succinates, benzoates, ascorbates, alpjha-keto-glutaric acid salts, maleates, fumarates, benzenesulfonates, and alpha-glycerin phosphates. These acids also form suitable inorganic salts, including hydrobromides, hydrochlorides, sulfates, nitrates, bicarbonates and carbonates.

The pharmaceutically acceptable salts can be obtained by common methods in the art, for example, a physiologically acceptable anion can be formed by reacting a compound with sufficient basic strength such as an amine with a suitable acid.

The compounds according to the invention can be administered in the form of pharmaceutical compositions comprising the compounds and appropriate carriers. These pharmaceutical compositions can be prepared by various processes and contain common carriers in the art. The guidelines for these processes and components have been taught in Remington's Pharmaceutical Sciences, edited by E. W. Martin (Mark Publ. Co., 15$^{th}$ Ed., 1975). For the necessity for the completeness of the invention, the reference document is introduced for reference. The compounds and the pharmaceutical compositions according to the invention can be administered non-enterogastrically (such as intravenously, intraperitoneally, intramuscularly), locally, transdermally, orally or rectally.

Mode of Carryng out the Invention

Figure 1:
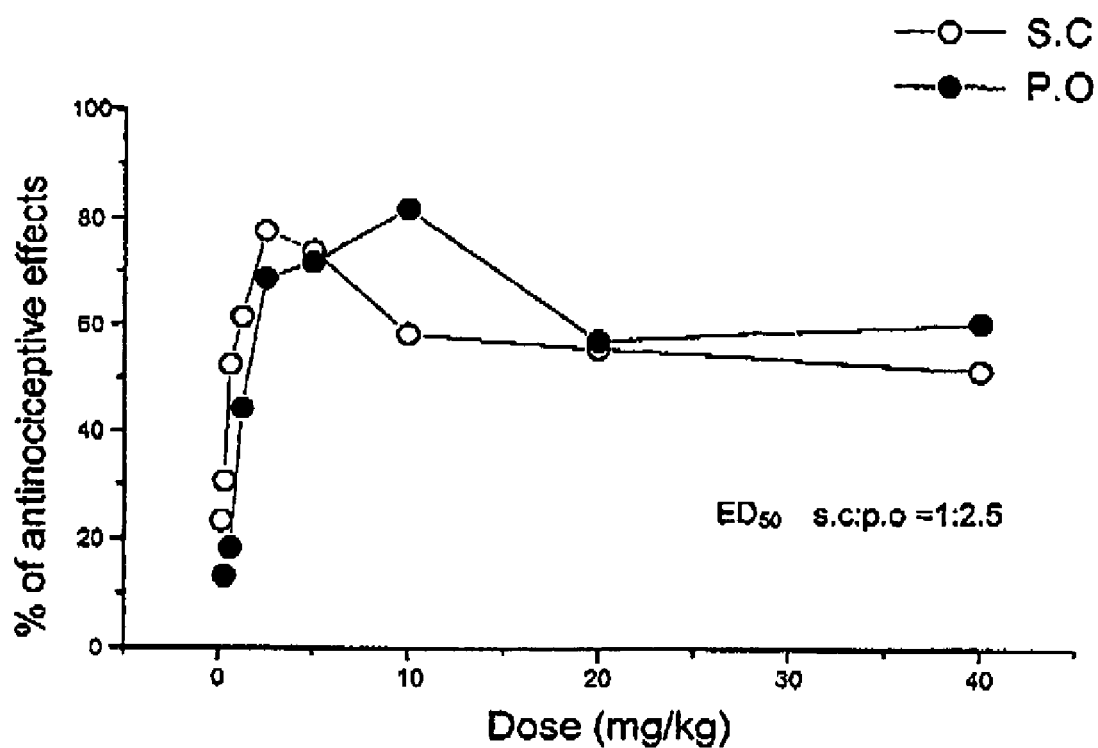
FIG. 1 is comparative curve of administering compound $I_1$ orally or by subcutaneous injection.

Following examples further describes the present invention, but not limit the invention at any way.

EXAMPLE 1

Preparation of 7α-acetyl-6,14-endoetheno tetrahydro thebaine (III)

49.8 g of thebaine (II) and 140 ml of methyl vinyl ketone were heated and refluxed for 1 hour. Excess methyl vinyl ketone was removed by distillation under reduced pressure. To the residue was added 60 ml of methanol and the mixture was heated to dissolve the residue. The resulting solution was cooled, the precipitated solid was filtered, and washed with cooled methanol and dried to give 56.3 g of a compound of formula III with a melting point of 118–120° C., the yield is 89%.

EXAMPLE 2

Preparation of 7α-acetyl-6,14-endoethano tetrahydro thebaine (IV)

The mixture of 19.2 g of the compound of formula III, 4 g of 10% Pd—C and 200 ml of absolute ethanol were hydrogenated at 50–60° C., 40–50 Kg/cm$^{-1}$ of hydrogen pressure for 8–12 hours. Upon the completion of the reaction, the catalyst was filtered off and the filtrate was concentrated and cooled. The precipitated solid was filtered, and washed with cooled ethanol and dried to give 15.4 g of a compound of formula IV with a melting point of 135–137° C., the yield is 80%.

EXAMPLE 3

Preparation of 7α-[(S)-1-hydroxy-1-methyl-3-(2-thiophenyl)-propyl]-6,14-endoethano tetrahydro thebaine (V)

The Grignard reagent was prepared by the reaction of 6.38 g (0.03 mol) of 2-thiophen-2-yl ethyl bromide and 4.9 g (0.2 mol) of magnesium in 100 ml of ether. To the Grignard reagent solution was added drop-wise a solution of 4.9 g (0.013 mol) IV in 100 ml of dried benzene. The mixture was heated and refluxed for 3 hours. Then the mixture was cooled to room temperature, and saturated ammonium chloride solution was added, extracted with ether, washed with water and then dried over $MgSO_4$. The solvent was removed under reduced pressure. The residue was recrystallized with methanol to give 4.54 g of a compound of formula V with a melting point of 183–185° C., the yield is 62%. By elemental analysis, $C_{29}H_{37}NO_4S$ has a theoretic value (%): C 70.30, H 7.47, N 2.83, experimental value (%) was C 70.18, H 7.56, N 2.74.

EXAMPLE 4

Preparation of N-cyano-7α-acetyl-6,14-endoethano tetrahydro-nor-thebaine (V')

1.6 g of cyanobromide was dissolved in 50 ml of chloroform, to the solution was added 5 g of the compound of formula IV, after refluxing for 12 hours, the solvent was removed under reduced pressure, the residue was recrystallized with absolute ethanol to give 3.2 g of a compound of formula V' with a melting point of 198–200° C., the yield is 62.3%.

EXAMPLE 5

Preparation of N-cyano-7α-[(S)-1-hydroxy-1-methyl-3-(thiophen-2-yl)-propyl]-6,14-endoethano tetrahydro-nor-thebaine (VI)

4.07 g (0.0385 mol) of cyanobromide was dissolved in 18 ml of dry methylene chloride; to the refluxing solution was added 4.54 g(0.0092 mol) of V in 18 ml of methylene chloride, after 4 hours of reaction, the solvent was removed by distillation. The residue was recrystallized with absolute ethanol to give 4.23 g of a compound of formula VI with a melting point of 171–173° C., the yield is 91.1%. By elemental analysis, $C_{29}1H_{34}N_2O_4S$ has theoretic value (%): C 68.77, H, 6.72, N, 5.53, and experimental value (%) was: C 68.81, H 6.72, N 5.40.

EXAMPLE 6

Preparation of 7α-acetyl-6,14-endoethano tetrahydro nor-thebaine (VI')

To 45 ml of 2 N hydrochloric acid was added 3.82 g of the compound of formula V', the mixture was refluxed for 2 hours and then cooled to 0° C.; to the cooled solution was added dropwise 0.78 g of sodium nitrite. The reaction was continued until there was no gas released, the reaction mixture was neutralized with ammonia to pH8–9 and extracted with chloroform, dried with $MgSO_4$. The solvent was removed under reduced pressure and the residue was recrystallized with methanol to obtain 1.46 g of a compound of formula VI' with a melting point of >300° C., the yield is 40.8%.

EXAMPLE 7

Preparation of 7α-[(S)-1-hydroxy-1-methyl-3-(2-thiophenyl)-propyl]-6,14-endoethano tetrahydro-nor-oripavine hydrochloride (VII)

To 4 g of the compound of formula VI was added 50 ml of diethylene glycol and 10 g of KOH. The mixture was stirred under $N_2$ at 190–200° C. for 1 hour. After finishing the reaction, the reaction mixture was poured into ice-water, and saturated ammonium chloride solution were added to adjust the pH 8–9, The produced solid precipitate was collected and recrystallized with methanol to yield 2.9 g of a compound of formula VII with a melting point of 268–270° C., the yield is 72%. By elemental analysis, $C_{27}N_{33}NO_4S.HCl.H_2O$ has a theoretic value (%) C 62.18, H 6.91, N 2.69; an experimental value (%) C 62.30, H 6.87, N 2.38.

EXAMPLE 8

Preparation of N-cyclopropyl-7α-acetyl-6,14-endoethano tetrahydro nor-thebaine (VII')

To 275 ml of DMF was added 11.82 g of the compound of formula VI', 5.43 ml of cyclopropyl methyl bromide and 6.4 g of sodium hydrocarbonate. The mixture was heated stirring under $N_2$ at 70° C. for 16 hours. The solid was filtered off, the filtrated was removed under reduced pressure, the residue was extracted with methylene chloride, dried with $MgSO_4$. The solvent was removed under reduced pressure. The residue was recrystallized with methanol to give 8.2 g of a compound of formula VII' with a melting point of 104–106° C., the yield is 60.74%.

EXAMPLE 9

Preparation of N-cyclopropyl-7α-[(S)-1-hydroxy-1-methyl-2-cyclopropyl-ethyl]-6,14-endoethano tetrahydro-nor-thebaine (VIII)

The Grignard reagent was prepared by the reaction of 1.2 g of cyclopropyl methyl bromide and 0.6 g of magnesium in 20 ml of ether. To the Grignard reagent solution was added drop-wise a solution of 0.88 g of the compound of formula VII' in 30 ml of dried ether. The mixture was heated and refluxed for 4 hours. Then the mixture was cooled to room temperature, and saturated ammonium chloride solution was added, the organic part was separated and the water part was extracted with ether 2 times, the organic solution was combined and dried with $Na_2SO_4$. The solvent was removed under reduced pressure and the residue was chromatographed on a silica gel column, the product obtained translated to hydrochloride with HCl-ether to give 0.55 g of a compound of formula VIII which was used for the next step without further purification.

EXAMPLE 10

Preparation of N-cyclopropylmethyl-7α-[(S)-1-hydroxy-1-methyl-3-(2-thiophenyl)-propyl]-6,14-endoethano tetrahydro-nororipavine hydrochloride ($I_1$)

To 210 ml of DMF was added 7 g (0.015 mol) of the compound of formula VII, 4.1 g (0.03 mol) of cyclopropyl methyl bromide, 3.95 g (0.047 mol) of sodium hydro carbonate. The mixture was heated stirring under $N_2$ at 70° C. for 16 hours. The solid was filtered off, the solvent of the filtrate was removed under reduced pressure, the residue was extracted with methylene chloride, dried with $MgSO_4$. The solvent was removed under reduced pressure. The residue was chromatographed on a silica gel column, recrystallized with methanol to give 3.79 g of the compound $I_1$ in the form of base in 48.4% yield, MP 170–172° C. Take 1.4 g of the product and dissolved with absolute ethanol, to the solution was added dropwise the ether solution of hydrochloride. The precipitated solid was collected and recrystallized with absolute ethanol to give 1.21 g of the compound $I_1$, melting pointing of 255–257° C. By elemental analysis, $C_{31}H_{38}NO_4S\cdot 2HCl\cdot 0.5\ H_2O$ has theoretic values (%): C 65.61 H 7.17 N 2.47 S 5.64, and an experimental value (%) of 65.53 H 7.18 N 2.07 S 5.41. IR: 3406 $cm^{-1}$ (w), $v_{as}$ $C_{19}$—OH; 3224 $cm^{-1}$ (w), $v_{as}$ $C_3$—OH; 2989, 2926 $cm^{-1}$ (m), γ, $C_{1,2}$—H,; 1634, 1609 $cm^{-1}$ (w), δ, ph-H, thiophenyl; 1080, 1023 $cm^{-1}$ (s), δ, C—N, C—O; 1023 $cm^{-1}$ (s), δ, cyclopropyl methyl; $^1$HNMR: δ (ppm, $CDCl_4$): 7.12–6.90 (dd, 2H, Ar—H); 6.85–6.50 (ddd, 3H, thiophenyl; 5.17 (s, 1H, 3-OH); 3.56 (s, 1H, 5β-H); 3.55 (s, 3H, 6-OCH3); 3.00–1.61 (m,15H, $C_{20,21,15,16,9,10}$, $C_{1',2'}$, $C_{19}$—OH); 1.40 (m, 3H, 19-$CH_3$);1.10–0.09 (m, 11H,$C_{17,18,7,8}$, $C_{3',4'}$); $^{13}$CNMR: δ (ppm, $CDCl_4$): 119.471 (1C, $C_1$); 116.511 (1C, $C_2$); 117.352 (1C, $C_3$); 145.547 (1C, $C_4$); 97.370 (1C, $C_5$); 80.506 (1C, $C_6$); 47.188 (1C, $C_7$); 31.599 (1C, $C_8$); 58.254 (1C, $C_9$); 43.636 (1C, $C_{10}$); 123.944 (1C, $C_{11}$); 132.211(1C, $C_{12}$); 45.686(1C, $C_{13}$); 35.880(1C, $C_{14}$); 35.607(1C, $C_{15}$); 75.771 (1C, $C_{16}$); 17.726 (1C, $C_{17}$); 29.763 (1C, $C_{18}$); 75.771 (1C, $C_{19}$); 43.454 (1C, $C_{20}$); 23.494 (1C, $C_{21}$); 23.236 (1C, $C_{19}$—$CH_3$);52.759 (1C, $C_6$—$OCH_3$); 146.004 (1C, $C_{22}$); 122.734(1C, $C_{23}$); 128.047 (1C, $C_{24}$); 126.666 (1C, $C_{25}$); 59.787 (1C, $C_{1'}$); 9.393 (1C, $C_{2'}$); 3.974, 3.484 (2C, $C_{3',4'}$)

EXAMPLE 11

Preparation of N-cyclobutyl-methyl-7α-[(S)-1-hydroxy-1-methyl-3-(2-thiophenyl)-propyl]-6,14-endoethano tetrahydro-nororipavine hydrochloride ($I_2$)

To 25 ml of DMF was added 1 g (0.002 mol) of the compound of formula VII, 0.64 g (0.0043 mol) of cyclobutyl methyl bromide, 0.53 g of sodium hydrocarbonate, and 0.1 g of NaI. The mixture was heated stirring under $N_2$ at 70° C. for 16 hours. The solid was filtered off, the solvent of the filtrate was removed under reduced pressure, the residue was extracted with methylene chloride, dried with $MgSO_4$. The solvent was removed under reduced pressure. The residue was chromatographed on a silica gel column. The product collected was dissolved with absolute ethanol, to the solution was added dropwise the ether solution of hydrochloride. The precipitated solid was collected and recrystallized with methanol to give 0.59 g of $I_2$ in 50.4% yield, MP 241–3° C. By elemental analysis, $C_{32}H_{40}NO_4S\cdot HCl\cdot 1.5H_2O$ has a theoretic value (%): C 64.27H 7.36 N 2.34 S 5.35, experimental value (%): C 65.10H 7.41 N 2.06 S 5.01.

EXAMPLE 12

Preparation of N-allyl-methyl-7α-[(S)-1-hydroxy-1-methyl-3-(2-thiophenyl) propyl]-6,14-endoethano tetrahydro-nor-oripavine hydrochloride ($I_3$)

To 205 ml of DMF was added 1.5 g (0.003 mol) of the compound of formula VII, 0.60 g (0.004 mol) of allyl bromide and 0.53 g of sodium hydrocarbonate. The mixture was heated stirring under $N_2$ at 70° C. for 16 hours. The solid was filtered off, the solvent of the filtrate was removed under reduced pressure, the residue was extracted with methylene chloride; dried With $MgSO_4$. The solvent was removed under reduced pressure. The residue was chromatographed on a silica gel column. The product collected was dissolved with absolute ethanol, to the solution was added dropwise the ether solution of hydrocloride. The precipitated solid was collected and recrystallized with methanol to give 0.35 g of the compound of $I_3$ with a melting point of 228–30° C., the yield is 22%. By elemental analysis, $C_{30}H_{36}NO_4S\cdot HCl$ has theoretic value (%): C 66.23H 7.00 N 2.58 S 5.89; experimental value (%) C 66.40 H 7.14 N 2.36 S 5.80.

EXAMPLE 13

Preparation of 7α-[(S)-1-hydroxy-1-methyl-3-(2-thiophenyl)-propyl]-6,14-endoethano tetrahydro-oripavine hydrochloride ($I_4$)

To 50 ml of diethylene glycol was added 4 g of the compound of formula V and 10 g of KOH. The mixture was stirred under $N_2$ at 190–200° C. for 1 hour and then was poured into ice-water. Saturated ammonium chloride solution were added to adjust pH 8–9. The precipitated solid was collected and recrystallized with methanol give 2.9 g of base of $I_4$ in 72 yield, MP 268–270° C. The base was translated to salt of hydrochloride with HCl-ether to give 3.1 g of a compound of formula $I_4$ with a melting point of >300° C. By element analysis, $C_{28}H_{34}NQ_4S\cdot HCl$ has theoretic value (%) C 64.86 H 6.95 N 2.70 S 6.18; experimental value (%): C 64.42H 7.22 N t 2.54 S 5.20.

EXAMPLE 14

Preparation of N-cyclopropylmethyl-7α-[(S)-1-hydroxy-1-methyl-2-cyclopropyl-ethyl]-6,14-endoethano tetrahydro-nor-oripavine hydrochloride ($I_5$)

To 8 ml of diethylene glycol was added 1.8 g of KOH. The mixture was heated under $N_2$ at 205–6° C. until the temperature stable. Then 0.55 g of the compound of formula VIII was added to the reaction mixture, stirred at the same temperature for 2 hours. The reaction mixture was poured into ice-water. Saturated ammonium chloride solution was added to adjust pH 8–9. The precipitated solid was collected and chromatographed on silica gel column. The product collected and made to salt of hydrochloride with HCl-ether, 0.16 g of a compound $I_5$ was obtained in 30% yield, melting pointing of 185–190° C. By element analysis, $C_{29}H_{40}NO_4\cdot HCl$ has theroretic value (%): C 69.25, H, 7.96, N, 2.79, S 6.37; experimental value (%): C 69.24, H, 7.72, N 2.45, S 6.68.

According to similar methods to prepare the compound $I_5$, N-cyclopropylmethyl-7α-[(S)-1-hydroxy-1-methyl-2-cyclopentyl-ethyl]-6,14-endoethano tetrahydro-nor-oripavine hydrochloride ($I_6$), with a melting point of 270° C., decomposed, was prepared by reaction of cyclopropyl methyl chloride compound via Grinard addition reaction. Also N-cyclopropylmethyl-7α-[(S)-1-hydroxy-1-methyl-cyclohexyl-ethyl]-6,14-endoethano tetrahydro-nor-oripavine hydrochloride ($I_7$), with a melting point of 241–6° C., decomposed, was prepared by reaction of cyclohexyl methyl chloride compound.

Experiment of Pharmacological Activity Evaluation

Pharmacological effect of the compounds according to the invention was measured by the methods of acetic acid writhing test, 55° C. hot plate test, rat 55° C. hot water bath test and so on.

1. Antinociceptive Tests 1.1. Methods (1) Mice 55° C. Hot plate Test (sc/po)

Female mice weighing 18–22 g were used in the test. The latency was measured as the period from placing the animals on the 55° C. plate to the appearance of response to the hot nociceptive stimulus (licking hindpaws, jumping and flicking of paws) before and after administration of drugs (sc/po), respectively. Each group had 8 mice. The cut off time was 60 sec. The results were expressed as possible maximal analgesic percentage (PMAP), $$PMAP = \frac{\text{Latency after administration} - \text{Latency before administration}}{60 - \text{Latency before administration}} \times 100$$

$ED_{50}$ was calculated with Logit program.

(2) Rat Hot Water Bath Test

Male and female (1:1) Wistar rats weighing 180–200 g were used. The latency was defined as a period from insertion of the tip part of the rat tail into 55° C. hot water to withdrawal of tail from it before and after administration of drugs, respectively. Each group had 8 mice. The results were expressed as PMAP and the computational method was same as that as mentioned above. The longest latency was defined as 15 s. And then $ED_{50}$ was calculated with Logit program.

(3) Acetic Acid Writhing Test

Male and female (1:1) mice weighing 18–22 g were used. Acetic acid (0.6%, 0.4 ml per mouse, ip) was administered to each animal. 5 min later, the frequency of writhing in the following 15 min was counted. The drugs or normal saline were administrated by sc 30 min and by po 60 min prior to injection of acetic acid, respectively. $ED_{50}$ was calculated with Logit program.

$$\text{analgesic percentage} = \frac{\text{writhing number in normal saline} - \text{writhing number in drug}}{\text{writhing number in normal saline}} \times 100$$

1.2 Results

TABLE 1

Antinociceptive activity of compounds

| Compounds | acetic acid writhing test | | hot plate test | |
|---|---|---|---|---|
| | $ED_{50}$ ($\mu g \cdot kg^{-1}$) | Max. efficacy (%) | $ED_{50}$ ($\mu g \cdot kg^{-1}$) | Max. efficacy (%) |
| $I_1$ | 116 | 100.0 | 860 | 81.7 |
| $I_2$ | Not determined | Not determined | 159 | 71.2 |
| $I_4$ | Not determined | Not determined | 15 | 100 |

In the mice hot plate test, analgesic dose-response curves of compound of compound $I_1$ was familiar with that of buprenorphine, Max. efficacy of which was less than 100%, which produced a dose-dependent partial agonist properties. Efficacy of compound of compound $I_1$ was stronger than that of buprenorphine, especially in serious analgesic models.

In the mice acetic acid writhing test, the Max. analgesic efficacy of compound $I_1$ reached 100% while that of buprenorphine was 92.5%. In the hot plate test, the Max. analgesic efficacy of compound $I_1$ was 81.7% while that of buprenorphine was 40.3% (Tab 1). In rat 55° C. hot water bath test and rat formaldehyde test, efficacy and potency of compound $I_1$ was stronger than that of buprenorphine (Tab 2). In the rhesus monkey tail flick test, the latency of tail flick was prolonged along with increasing of dose when given compound $I_1$ 16 $\mu g \cdot kg^{-1}$ im or 6–24 $\mu g \cdot kg^{-1}$ po, but the effects of the latter was weaker than that of former (Tab 4). From above results, compound $I_1$ showed preferable antinociceptive activity.

TABLE 2

Antinociceptive activity of compounds

| Compounds | writhing test | | hot plate test | |
|---|---|---|---|---|
| | $ED_{50}$ ($\mu g \cdot kg^{-1}$) | Max. efficacy (%) | $ED_{50}$ ($\mu g \cdot kg^{-1}$) | Max. efficacy (%) |
| $I_5$ | 6.39 | 100.0 | 200 | 71.2 |
| $I_6$ | 55.9 | 100 | 50 | 54.2 |
| $I_7$ | Not determined | Not determined | 159.1 | 94 |
| Bup | 7.3 | 90 | 1100 | 40 |

In the mice hot plate test, efficacy and potency of compound $I_5$–$I_7$ was stronger than that of buprenorphine, Max. analgesic efficacy of which were less than 100%, producing a dose-dependent partial agonist properties.

TABLE 3

Comparison of Antinociceptive effects of compounds $I_1$ and buprenorphine in rats

| Compounds | hot water bath test | | formaldehyde test | |
|---|---|---|---|---|
| | $ED_{50}$ ($mg \cdot kg^{-1}$) | Max. efficacy (%) | $ED_{50}$ ($mg \cdot kg^{-1}$) | Max. efficacy P (%) |
| buprenorphine | 8.75 | 64.7 | 0.34 | 97.7 |
| $I_1$ | 3.48 | 79.3 | 0.15 | 100.0 |

TABLE 4

Analgesic effect of compound $I_1$ in the rhesus monkey tail flick test

| Dose µg · kg$^{-1}$ | Pathway of administration | Latency tail flick (X ± SD, sec) | Dose µg · kg$^{-1}$ | Pathway of administration | latency (X ± SD, sec) |
|---|---|---|---|---|---|
| 0 | Im | 3.5 ± 0.2 | 0 | po | 4.0 ± 0.7 |
| 1 | Im | 4.8 ± 2.1 | 6 | po | 5.1 ± 1.8 |
| 2 | Im | 6.5 ± 3.6 | 12 | po | 6.0 ± 1.9 |
| 4 | Im | 7.9 ± 2.5* | 24 | po | 6.7 ± 2.3* |
| 6 | Im | 9.2 ± 3.1* | 48 | po | 5.7 ± 0.5* |

*$P < 0.05$, Comparison with 0 µg · kg$^{-1}$ group; n = 5

In mice hot plate test, analgesic effects of the compound $I_1$ administered by po and sc, was compared (see FIG. 1). The $ED_{50}$ value po was 2.5 times of that of sc, but the Max. efficacy of them was almost identical. In the same test, the $ED_{50}$ value of buprenorphine po was 12.4 times of that of sc. In other analgesic models, the ratio of $ED_{50}$ value po/$ED_{50}$ value sc of compound $I_1$ was less than that of buprenorphine (Tab 4). The above results indicated that bioavailability of compound $I_1$ was higher than that of buprenorphine, the range of effective dose of compound $I_1$ was 1–3 mg·kg$^{-1}$ in two analgesic models.

2. Physical Dependent Test

2.1. Methods and Animals

Male Swiss mice, weighing 18–22 g, pretreated with morphine (24 mg·kg$^{-1}$, s.c.) or buprenorphine (3.6 mg·kg$^{-1}$, s.c.) or compound $I_1$ (5.0 mg·kg$^{-1}$, s.c.) respectively 3 times daily for 14d, naloxone(10 mg·kg$^{-1}$, i.p.) was injected 4 h after the last administration of drugs, The number of jumping was immediately observed within a period of 15 min and loss of body weight were marked 60 min after administration of naloxone.

Wister rats, male, weighing 180–200 g, were used. Morphine, buprenorphine and compound $I_1$ were administered as mentioned above. 4 h after the last administration of drugs, all subjects were injected naloxone(5 mg·kg$^{-1}$ s.c.). The frequency of gasps, ptosis, shakes, teeth chatter and yawns was immediately observed for 15 min after injection of naloxone. The total score for abstinence signs was calculated as the sum of the scores for all individual signs of the withdrawal reaction. Loss of body weight was recorded for 60 min after injection of naloxone.

2.2. Results

There was a significant increase in the number of total abstinence signs in morphine-treated group (30×Tid×7d, 30×Tid×14d) compared with saline group Statistical evaluation of these data showed no significant differences in the number of abstinence syndrome in compound $I_1$-treated mice compared with saline group. These data indicated that compound $I_1$ has low potency of dependence.

TABLE 5 comparison of the analgesic effect of compound by s.c. and p.o. administration in mice.

| Methods of test | Compound | $ED_{50}$ (mg/kg) S.C | $ED_{50}$ (mg/kg) P.O | P.O/S.C |
|---|---|---|---|---|
| Acetic Writhing | Buprenorphine | 0.02 | 0.37 | 17.6 |
|  | $I_1$ | 0.08 | 0.64 | 8.2 |
| Hot plate | Buprenorphine | 1.01 | 12.52 | 12.4 |
|  | $I_1$ | 0.57 | 3.10 | 5.4 |
| tail-flick | Buprenorphine | 8.75 | —* | Not detectable |
|  | $I_1$ | 1.75 | 2.61 | 1.5 |

*<30%

TABLE 6 comparison of the experimental results on the physical dependence in mice

| Compound | Dose (mg · kg$^{-1}$) | Percent of (%) | Number of jumping | loss weight (g) |
|---|---|---|---|---|
| Saline | — | 20 | 2.1 ± 3.0 | 0.4 ± 0.4 |
| Morphine | 24.0 × Tid × 14d | 100 | 49.5 ± 56.0** | 1.6 ± 0.2** |
| Buprenorphine | 3.6 × Tid × 14d | 80 | 14.6 ± 27.4* | 0.8 ± 0.2 |
| $I_1$ | 5.0 × Tid × 14d | 0 | 0 ± 0 | 0.5 ± 0.2 |

2. Psychological Dependence Experiment (1) Conditioned Place Preference Testing in Mice Swiss mice, male, weighted 18–22 g. Animals were immediately confined for 40 min to one compartment after injection of compound $I_1$, and to the other compartment after injection of saline. Animals that had been injected with drugs were confined to one of the end compartments A.M, and to the other of the end compartments after the injection of saline P.M. This tendentious conditioning cycle was performed for 5 d. On day 6, preference state, after placing the animals in the neutral middle compartment and allowing them free access to each compartment. The time spent in drug-paired compartment was measured.

The results are shown in Table 7. As seen in Table 7, morphine (10 mg·kg$^{-1}$) and buprenorphine (0.3 mg·kg$^{-1}$) and compound $I_1$ (3 and 10 mg·kg$^{-1}$) induced significant Conditioned Place Preference.

TABLE 7 comparison of the experimental results on the physical dependence in rats

| Compound | Dose (mg·kg$^{-1}$) | Score of withdrawal symptoms(%) | loss weight (g) |
|---|---|---|---|
| Saline | — | 1.8 ± 1.3 | 1.4 ± 0.6 |
| Morphine | 30 × Tid × 7d | 8.0 ± 2.2** | 12.0 ± 2.6** |
| Buprenorphine | 5 × Tid × 7d | 4.0 ± 2.0 | 4.2 ± 2.5 |
| I$_1$ | 3 × Tid × 7d | 2.2 ± 1.3 | 0.4 ± 0.6 |
| Saline | — | 1.8 ± 1.3 | 2.8 ± 1.3 |
| Morphine | 30 × Tid × 14d | 6.4 ± 2.2** | 4.2 ± 1.2 |
| Buprenorphine | 5 × Tid × 14d | 3.6 ± 1.1 | 4.2 ± 1.3 |
| I$_1$ | 3 × Tid × 14d | 2.8 ± 0.8 | 2.0 ± 1.9 |

TABLE 8

Experimental results of conditional place preferencein mice

| Compound | Dose (mg/kg) | Time spent in drug-paired place (min) |
|---|---|---|
| Saline | — | 316.2 ± 119.6 |
| Morphine | 10 | 566.6 ± 131.1** |
| Buprenorphine | 0.3 | 547.5 ± 175.0** |
| I$_1$ | 1 | 415.3 ± 119.2 |
|  | 3 | 452.3 ± 66.6* |
|  | 10 | 474.0 ± 136.4* |

(2) Self-administration Testing

The subjects were male Wistar rats, 350–400 g and rhesus monkey, 4–6 kg at the start of the experiments. Anesthesia was induced by administration of sodium pentobarbital (40 mg·kg$^{-1}$, i.p). While anesthetized, rats were implanted with guide cannulas, one end of guide cannulas was implanted right atrium, and the other end was connected with self-administration installation. Penicillin Gi was administered immediately after surgery.

Self-administration sessions were began 3 days after surgery. Rats were trained to self-administration compound I$_1$ at a dose of 0.1 mg·kg$^{-1}$ infusion on FR1 schedule. Daily sessions were 6 h. In duration, the number of infusions was recorded, while animals were deprived food.

The results indicated that compound I$_1$ (0.05, 0.08, 0.1 mg·kg$^{-1}$) couldn't induce self-administration in rat in continuous 35–40 days session (daily injections <10). Opiate receptor partial agonist buprenorphine also couldn't induce self-administration. Compound I$_1$ (0.025–0.05 mg·kg$^{-1}$/inject) couldn't induce the development of self-administration in rhesus monkey. These data indicate that the potency of dependence of compound I$_1$ is weak.

3. Substitution Test (1) Methods and Animals

Methods and animals were as similar to self-administration test. Heroin was substituted by compound I$_1$ after development of stable self-administration induced by heroin in rat. Step number and rating was recorded.

Stable self-administration was developed by morphine (0.25 mg·kg$^{-1}$/inject) in rhesus monkey. Compound I$_1$ (0.025 mg·kg$^{-1}$/inject), morphine (0.25 mg·kg$^{-1}$ mg·kg$^{-1}$/inject), buprenorphine (0.05 mg·kg$^{-1}$/inject), morphine (0.25 mg·kg$^{-1}$/inject) and compound I$_1$ (0.05 mg·kg$^{-1}$/inject) was substituted by turns.

(2) Results

Self-administration could continue induced by compound I$_1$ in heroin dependent rat. There were not increases of step number of 3 rats, but increased in other 3 rats. Step numbers were decreased in most of rat compared with the treatment of heroin.

Compound I$_1$ (0.025 mg·kg$^{-1}$/inject) could continue self-administration in the place of morphine (0.25 mg/kg/inject), so did buprenorphine. Compound I$_1$ (0.05 mg·kg$^{-1}$/inject) could not maintain this test in replace of morphine (0.25 mg·kg$^{-1}$/inject) or buprenorphine (0.05 mg·kg$^{-1}$/inject). Results inferred that compound I$_1$ had potency of addict, was as similar as buprenorphine, and was weaker than morphine.

4. Na$^+$ Index Determination (1) Methods

The subjects were male wistar rats, weighing 180–200 g. Rats were sacrificed by decapitation. The brain of rats without cerebellum was used to make membrane preparation containing opiate receptors, The brain was homogenized in 50 mmol·L$^{-1}$ tris-HCL solutions and centrifuged (20,000 rev/min, 20 min). This procedure was repeated twice more. Each assay contained 0.5 mg membrane protein, 5 nmol·L$^{-1}$ 3H-naloxone and different concentrations of drugs (1–1100000 nmol·L$^{-1}$). Nonspecific binding was determined in the presence of 10 μmol·L$^{-1}$ naloxone. The IC$_{50}$ was calculated with Logit method. The Na$^+$ index was determined by the ratio of the IC$_{50}$ in the presence of 100 nmol·L$^{-1}$ NaCl to those in absence of it, (2) Results Compound I$_1$ could inhibit $^3$H-naloxone binding with opiate receptors as similar to morphine and buprenorphine. The affinity of formula It to opiate receptors was higher 100 times than that of morphine. Na$^+$ index is 0.42, which is character of typical antagonist.

TABLE 9

Influence of Na$^+$ in competitive inhibition of drugs on binding affinity with opiate receptors of rat brain

| Compound | IC$_{50}$ (nmol·L$^{-1}$) Free of Na$^+$ | IC$_{50}$ (nmol·L$^{-1}$) Presence of Na$^+$ | Na$^+$ index |
|---|---|---|---|
| Morphine | 18 | 170 | 9.44 |
| Buprenorphine | 0.45 | 0.30 | 0.67 |
| I$_1$ | 0.19 | 0.08 | 0.42 |

In all, we have described this invention in detail by using preferred embodiments of the invention. Obviously, it is allowed to improve and transform the invention at the premise of undeviating from privilege of the invention.

We claim:

1. An oripavine compound represented by formula (I),

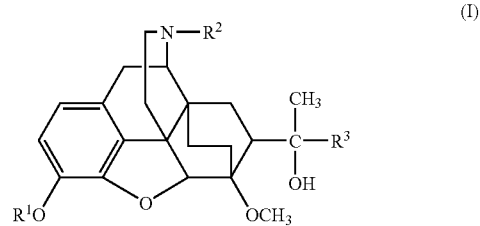

wherein R¹ is hydrogen or methyl, R² is methyl, cyclopropyl methyl, cyclobutyl methyl or allyl, R³ is thiophenyl ethyl, or a non-toxic pharmaceutically acceptable salt thereof.

2. The oripavine compound or non-toxic pharmaceutically acceptable salt thereof according to claim 1, characterized in that the compound is represented by the following formula:

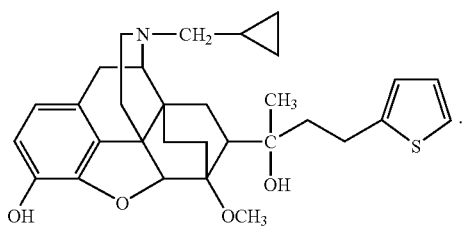

3. The oripavine compound or non-toxic pharmaceutically acceptable salt thereof according to claim 1, characterized in that the compound is represented by the following formula:

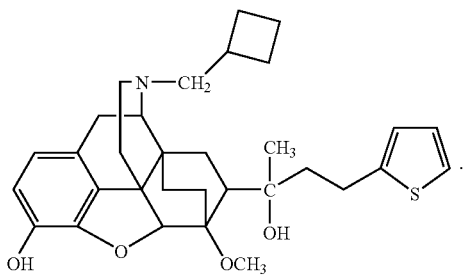

4. The oripavine compound or non-toxic pharmaceutically acceptable salt thereof according to claim 1, characterized in that the compound is represented by the following formula:

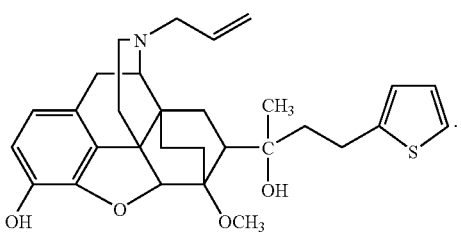

5. The oripavine compound or non-toxic pharmaceutically acceptable salt thereof according to claim 1, characterized in that the compound is represented by the following formula:

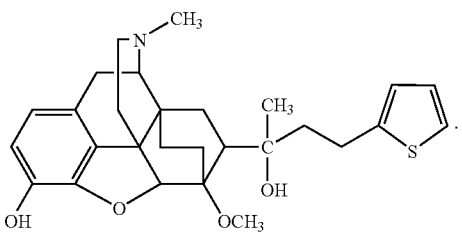

6. A pharmaceutical composition comprising as active ingredient a therapeutically effective amount of a oripavine compound or non-toxic pharmaceutically acceptable salt thereof according to any one of claims 1, 2 or 3–5 and pharmaceutical acceptable carriers.

7. A method for treating pain by administering an oripavine compound or non-toxic pharmaceutically acceptable salt thereof according to any one of claims 1, 2 or 3–5 to an animal in need thereof.

8. A method for treating addiction to opium habit forming drugs by administering an oripavine compound or non-toxic pharmaceutically acceptable salt thereof according to any one of claims 1, 2 or 3–5 to an animal in need thereof.

* * * * *